United States Patent [19]
Yoshii

[11] Patent Number: 4,505,673
[45] Date of Patent: Mar. 19, 1985

[54] ORTHODONTIC TREATING DEVICE AND METHOD OF MANUFACTURING SAME

[75] Inventor: Osamu Yoshii, Chofu, Japan

[73] Assignee: Hito Suyehiro, Rockville, Md.

[21] Appl. No.: 845,619

[22] Filed: Oct. 26, 1977

[30] Foreign Application Priority Data

Nov. 5, 1976 [JP] Japan .................. 51-132323

[51] Int. Cl.³ ............................... A61C 7/00
[52] U.S. Cl. .................................. 433/6
[58] Field of Search ............. 260/29.1 SB; 528/11, 528/24, 32; 32/14 B, 14 C

[56] References Cited

U.S. PATENT DOCUMENTS

| | | | |
|---|---|---|---|
| 2,467,432 | 4/1949 | Kesling | 32/14 B |
| 3,316,640 | 5/1967 | Kesling | 32/14 B |
| 3,478,429 | 11/1969 | Shilliday | 32/14 C |
| 3,898,736 | 8/1975 | Bergersen | 433/6 |
| 3,950,851 | 4/1976 | Bergersen | 32/14 B |
| 4,016,328 | 4/1977 | Horning | 260/29.15 B |
| 4,022,747 | 5/1977 | Itoh | 260/29.15 B |
| 4,139,944 | 2/1979 | Bergersen | 433/6 |

Primary Examiner—Robert Peshock
Attorney, Agent, or Firm—Armstrong, Nikaido, Marmelstein & Kubovcik

[57] ABSTRACT

Original models of plaster are obtained from impressions of the dentition of the upper and lower jaws of a patient with malocclusion. The teeth are then separated from the base of the models and reset in wax to a normal occlusion. The realigned teeth are fixed in place with wax, and impressions of the upper and lower models are taken to duplicate the rearranged models, forming working models made of plaster. The working models are mounted on an anatomic dental articulator and a wax occluding model is constructed of the new occlusion to cover both upper and lower arches. The working upper and lower models, together with the wax occluding model are buried in plaster in a split cast. The wax occluding model in the split cast is heated and the wax is melted and discharged out of the cast. Silicone resin is then placed into the impression of the occluding model and cured.

6 Claims, 16 Drawing Figures

ORTHODONTIC TREATING DEVICE AND METHOD OF MANUFACTURING SAME

BACKGROUND OF THE INVENTION

Conventional orthodontic treatment is accomplished with metal bands provided with an attachment made to adapt to the teeth and is fixed to the teeth with cement, and metal wire is made to run through it to move the teeth. In this case, the correcting force (stress to move the teeth) primarily utilizes the elastic forces of the metal wire itself, and it is generally widely used as the orthodontic treating device.

However, in the orthodontic treatment using this multibanded technique with the bending of the metal wire in complicated shapes, it has been recognized that tremendous amounts of energy and skill as well as long periods of education are needed. Also, such treatment not only causes discomfort to the patient, but also other problems such as decayed or decalcified teeth or periodontal disease result from food particles adhering to the teeth during the orthodontic treatment, and, moreover, costs rise enormously.

The present invention has been conceived with a view to manufacturing an orthodontic treating device by which a malocclusion can be treated simply by utilizing the elastic force of silicone resins as a functional force instead of the metal wire presently being employed, and since it is easily detachable, it does not render any discomfort to the patient, making it possible to accomplish the orthodontic treatment when used at bedtime and waking hours as needed.

First, it is necessary to select an elastic high molecular material that satisfies sufficiently the special and severe conditions of intraoral treatment. The applicants have found that silicone resins are an elastic material suitable for orthodontic treatment bringing about the best results from the standpoint of science, engineering and clinical study. Namely, the material has been recognized to have scientific and engineering quality so that it does not deteriorate in its elasticity while in the mouth, has sufficient breaking stress, and does not deform for long periods of time due to force during treatment. Because of these important properties, the treating device of the present invention can be used to treat patients from the initial stages until completion of treatment.

Moreover, by changing the hardener portion of the silicone resins and catalysts and the blending thereof, hardness of the molded silicone resin can be changed freely. Forces can be provided from a light force to a strong force which is advantageous from the clinical standpoint. The device maintains a high degree of transparency without having any taste or odor, and is prepared from a composition which causes no harm to the human body. These properties cannot be found in other rubber materials.

In addition to the silicone resin, polyurethane resins have somewhat similar qualities mentioned above, but silicone resins provide additional advantages such as shorter hardening processing time as compared with the polyurethane resin, and the manufacturing process can be accomplished simply, and therefore a remarkable difference is recognized between the two resins. In addition, where polyurethane resins are used to prepare similar devices, such resins break down in the patient's mouth and are not transparent. Therefore, such devices are only used during the final stages of treatment and cannot be used from the initial stage.

Accordingly, the applicants have discovered that the treating device of the present invention made from silicone resins for the first time, provides a means of treating a patient from the beginning to completion. To date, this has only been possible through the known procedure of using metal bands.

The present invention is directed to providing an orthodontic treating device and method of making, which ultimately utilizes characteristics of the silicone resin mentioned above.

BRIEF DESCRIPTION OF DRAWINGS

FIG. 8 is a comparison view showing before and after the orthodontic treatment and 8A shows before and 8B shows after the treatment.

FIG. 9 shows the first embodiment of the present invention, and 9A shows an end view of the condition where a split-cast (9) is separated, and 9B shows an end cross sectional view of the condition where the silicone resin is filled in the split-cast, and 9C shows an end cross sectional view of the condition where the separated portions of the split-cast are joined.

FIG. 10 shows a second embodiment of the present invention, and 10A shows a top view of an anatomical articulator, and 10B shows a side view of the condition where the wax plate material necessary to fix the upper and lower plaster models is melted and discharged, and 10C shows a side view of the condition where the silicone resin is pressure contacted on the surface of the working model to produce the orthodontic treating device, and 10D shows a cross sectional view taken along a line X—X of 10A.

SUMMARY OF THE INVENTION

The present invention is directed to a first method of making a silicone resin orthodontic treating device by (a) preparing plaster models of a patient's upper and lower jaw including the teeth showing malocclusion, (b) determining the centric relationship between the patient's upper and lower teeth by taking a wax impression, (c) taking a face-bow transfer of the patient's upper teeth to establish the relationship of the upper jaw to the head and face, (d) placing the face-bow in an anatomical articulator, (e) positioning the upper and lower models of step (a) in the anatomical articulator using the face-bow and the wax bite of step (b) to reproduce the patient's upper and lower jaw relationship and fixing the models in plaster such that the models are attached to the articulator, (f) removing the teeth from the models and realigning the teeth in wax to normal occlusion, (g) duplicating the normal occlusion of the models with a duplicating material to form negative impressions, (h) forming positive plaster models from the negative impressions, (i) opening the articulator to form a space of from 3 to 5 mm between the upper and lower incisor edge, (j) placing wax in the space to obtain an impression of the upper and lower teeth in normal occlusion, (k) placing the teeth of the upper and lower plaster models of step (h) into the wax impression of step (j), (l) covering the resulting combination of step (k) with wax such that the wax will have substantially the same shape and thickness as the silicone resin treating device, (m) flasking the wax covered model combination of step (l) in a split-cast, (n) subjecting the split-cast containing the wax covered model to heat sufficient to melt the wax and produce a void, (o) removing the wax, (p) filling the void with silicone resin and curing the resin, and (q) removing the silicone resin treating device.

The invention is also directed to a second method for producing the silicone resin orthodontic treating device by substantially repeating steps (a)–(h) as set forth above including the additional steps of: (i) removing the wax models from the articulator and replacing them with the plaster models of step (h) while maintaining the same upper and lower jaw relationship, (j) opening the articulator to form a space of 3 to 5 mm between the upper and lower incisor edge, (k) forming heat-curable silicone resin around the upper and lower teeth and curing the resin and (l) removing the resulting treating device.

Although either of the above-identified procedures may be used to make the orthodontic treating device of the present invention, the first method is preferred, since it provides the means of using adequate pressure to force the silicone resin into every crevice surrounding the teeth and the resulting treating device provides an accurate duplication of the patient's teeth in normal occlusion.

DETAILED DESCRIPTION OF THE PREFERRED EMBODIMENTS

The present invention is accomplished in a process employing the following steps:

(a) Preparing plaster models of the patient's upper and lower jaw including the teeth showing malocclusion.

An impression is taken of the patient's upper and lower teeth and surrounding tissue by using a duplicating material to obtain a negative impression. The duplicating material is removed from the teeth and a void is formed in the material. Plaster is poured into the void of the negative impression to obtain a positive plaster mold of the patient's upper and lower teeth.

(b) Determining the centric relationship between the patient's upper and lower teeth by taking a wax impression.

Wax is placed between the patient's upper and lower teeth to obtain an imprint of the bite to determine the centric relationship of the upper and lower teeth. This wax impression is used later in the process to properly align the upper and lower plaster models prepared in step (a).

(c) Taking a face-bow transfer of the patient's upper teeth to establish and reproduce the relationship of the upper jaw to the head and face.

A face-bow is used to take a wax impression of the patient's upper teeth to reproduce the upper jaw relationship to the head and face. This step is critical to the process of the invention, since it provides the only means of accurately reproducing the ultimate relationship of the patient's upper and lower jaw and this procedure serves the basis for properly aligning the plaster models from which the orthodontic treating device is to be prepared. The device must have the same upper and lower jaw relationship as that of the patient such that, when the device is used, the relationship of the teeth will properly fit into the device to cause the teeth to move towards normal occlusion.

(d) Placing the face-bow in an anatomic articulator.

The face-bow with the wax impression of the patient's upper teeth is attached to an anatomical articulator to properly align the upper and lower plaster models.

(e) Positioning the upper and lower models of step (a) in the anatomic articulator using the face-bow and the wax bite of step (b) to reproduce the patient's upper and lower jaw relationship and fixing the models in plaster such that the models are attached to the articulator.

This procedure is accomplished by placing the teeth of the upper plaster model as prepared in step (a) into the wax impression of the face-bow which has been attached to the anatomical articulator. Plaster is placed on top of the upper model and forced against the top of the articulator and permitted to dry, thereby, causing the upper model to be attached to the top of the articulator. Once the plaster has become dry, the face-bow is removed from the articulator. The upper model has now been placed into the articulator in the same relationship as the natural position of the patient's upper teeth and jaw.

The wax bite impression as prepared in step (b) is placed over the teeth of the upper model and luted or attached. The lower plaster model from step (a) is inserted into the lower portion of the wax impression which is attached to the upper model. Plaster is poured over the surface of the lower model and the articulator is closed and the plaster permitted to dry such that the lower model becomes attached to the articulator.

Up to this point in the process of the invention, the upper and lower plaster models have been attached to the articulator in the manner such that an exact reproduction of the patient's jaw and teeth relationship has been established.

(f) Removing the teeth from the models and re-aligning the teeth in wax to normal occlusion.

The plaster teeth are individually removed from the plaster model by means of a thin blade saw. Then, wax material is placed upon the base of the plaster models from which the individual teeth have been removed and the teeth are placed into the wax and arranged in normal occlusion. At this point, the upper and lower models have the teeth positioned in the manner such that the silicone resin orthodontic treating device to be made from the process of the invention will move the teeth to the position formed by the wax models.

(g) Duplicating the normal occlusion of the models with a duplicating material to form negative impressions.

A duplicating material is formed around the wax models to form negative impressions in normal occlusion. The material is removed from the models and the impressions show voids of the teeth in normal occlusion.

(h) Forming positive plaster models from the negative impression.

Plaster is poured into the voids of the negative impression to prepare positive plaster models which show the position of the patient's teeth after treatment with the orthodontic treating device made by the process of the invention.

(i) Opening the articulator to form a space of from 3 to 5 mm between the upper and lower incisor edge.

The articulator is opened such that a space is formed of from 3 to 5 mm, preferably 4 mm, between the upper and lower incisor edge. This space is necessary to properly form the orthodontic treating device in that the silicone resin will fill the space between the teeth and when the patient bites down on the resin during orthodontic treatment, the biting force and the resilience of the resin assist in moving the teeth.

(j) Placing wax in the space to obtain an impression of the upper and lower teeth in normal occlusion.

This step is necessary to obtain the proper relationship between the upper and lower teeth. This impression will be later used to replace the wax models with the plaster models of step (h) in the articulator.

(k) Placing the teeth of the upper and lower plaster models of step (h) into the wax impressions of step (j).

The plaster models in normal occlusion as prepared in step (h) are placed into the wax impression as obtained in step (j). The wax impression is employed to properly align the upper and lower plaster models. This combination or assembly is accomplished separately and outside of the articulator.

(l) Covering the resulting combination of step (k) with wax such that the wax will have substantially the same shape and thickness as the silicone resin treating device.

Wax is placed over the entire teeth surface areas and the portion representing the tissue of the upper and lower models which includes the wax material placed between the teeth in step (k). The wax material should have substantially the same shape and thickness as the silicone resin treating device which is to be prepared during the process as will hereinafter be explained.

(m) Flasking the wax covered model combination of step (l) in a split-cast.

The combination as prepared in step (l) is placed into the lower half of a split-cast and plaster is poured into the cast to cover the entire lower half of the combination model. The plaster is permitted to dry and harden and a separating medium is applied over the hardened plaster layer.

The split-cast is turned over and plaster is poured into the cast and the cast is closed such that the exposed upper portion of the combination is totally embedded into the soft plaster. Sufficient plaster should be used so that the plaster covers the entire surface of the combination model as evidenced by excess plaster flowing out of the cast. The cast is then clamped closed and the plaster permitted to dry.

(n) Subjecting the split-cast containing the wax covered model to heat sufficient to melt the wax and produce a void.

The entire split-cast containing the model as prepared in step (m) is heated such as by placing into boiling water for a time sufficient to melt the wax.

(o) Removing the wax.

The split-cast is opened and the melted wax is removed leaving a void around the teeth and tissue of the plaster model including the space between the upper and lower teeth.

(p) Filling the void with heat-curable silicone resin and curing the resin.

A soft silicone resin material is placed into the void in amounts sufficient to completely fill the void. The cast is closed tightly such that the resin material will fill every space and crevice completely and excess material will flow out of the void. The split-cast is then subjected to heat such as boiling water for a period of about 40 minutes to cure the silicone resin material.

(q) Removing the silicone resin treating device.

The split-cast is removed, cooled, opened and the resulting silicone resin orthodontic treating device is removed.

As a final step, the resulting treating device may be coated with a silicone resin solution containing two different silicone resins, including a catalyst, to provide a clear, invisible smooth surface. The two solutions are mixed in a ratio of about 10 to 1. The procedure discussed above is the preferred method, since the treating device is made as a result of using a split-cast to force the silicone resin into each space and crevice of the void in the plaster model.

In a second embodiment of the invention, a similar process is employed, except that only steps (a) through (h) of the former process are repeated. The second embodiment is accomplished by the following steps:

(a) Preparing plaster models of the patient's upper and lower jaw including the teeth showing malocclusion.

An impression is taken of the patient's upper and lower teeth and surrounding tissue by using a duplicating material to obtain a negative impression. The duplicating material is removed from the teeth and a void is formed in the material. Plaster is poured into the void of the negative impression to obtain a positive plaster mold of the patient's upper and lower teeth.

(b) Determining the centric relationship between the patient's upper and lower teeth by taking a wax impression.

Wax is placed between the patient's upper and lower teeth to obtain an imprint of the bite to determine the centric relationship of the upper and lower teeth. This wax impression is used later in the process to properly align the upper and lower plaster molds prepared in step (a).

(c) Taking a face-bow transfer of the patient's upper teeth to establish and reproduce the relationship of the upper jaw to the head and face.

A face-bow is used to take a wax impression of the patient's upper teeth to reproduce the upper jaw relationship to the head and face. This step is critical to the process of the invention, since it provides the only means of accurately reproducing the ultimate relationship of the patient's upper and lower jaw and this procedure serves the basis for properly aligning the plaster models from which the orthodontic treating device is to be prepared. The device must have the same upper and lower jaw relationship as that of the patient such that, when the device is used, the relationship of the teeth will properly fit into the device to cause the teeth to move towards normal occlusion.

(d) Placing the face-bow in an anatomic articulator.

The face-bow with the wax impression of the patient's upper teeth is attached to an anatomical articulator to properly align the upper and lower plaster models.

(e) Positioning the upper and lower models of step (a) in the anatomic articulator using the face-bow and the wax bite of step (b) to reproduce the patient's upper and lower jaw relationship and fixing the models in plaster such that the models are attached to the articulator.

This procedure is accomplished by placing the teeth of the upper plaster model as prepared in step (a) into the wax impression of the face-bow which has been attached to the anatomical articulator. Plaster is placed on top of the upper model and forced against the top of the articulator and permitted to dry, thereby, causing the upper model to be attached to the top of the articulator. Once the plaster has become dry, the face-bow is removed from the articulator. The upper model has now been placed into the articulator in the same relationship as the natural position of the patient's upper teeth and jaw.

The wax bite impression as prepared in step (b) is placed over the teeth of the upper model and luted or attached. The lower plaster model from step (a) is inserted into the lower portion of the wax impression which is attached to the upper model. Plaster is poured over the surface of the lower model and the articulator is closed and the plaster permitted to dry such that the lower model becomes attached to the articulator.

Up to this point in the process of the invention, the upper and lower plaster models have been attached to the articulator in the manner such that an exact reproduction of the patient's jaw and teeth relationship has been established.

(f) Removing the teeth from the models and re-aligning the teeth in wax to normal occlusion.

The plaster teeth are individually removed from the plaster model by means of a thin blade saw. Then, wax material is placed upon the base of the plaster models from which the individual teeth have been removed and the teeth are placed into the wax and arranged in normal occlusion. At this point, the upper and lower models have the teeth positioned in the manner such that the silicone resin orthodontic treating device to be made from the process of the invention will move the teeth to the position formed by the wax models.

(g) Duplicating the normal occlusion of the models with a duplicating material to form negative impressions.

A duplicating material is formed around the wax models to form negative impressions in normal occlusion. The material is removed from the models and the impressions show voids of the teeth in normal occlusion.

(h) Forming positive plaster models from the negative impression.

Plaster is poured into the voids of the negative impression to prepare positive plaster models which show the position of the patient's teeth after treatment with the orthodontic treating device made by the process of the invention.

(i) Removing the wax models from the articulator and replacing them with the plaster models of step (h) while maintaining the same upper and lower jaw relationship.

The duplicated plaster models as prepared in step (h) are mounted on the articulator in accordance with the following steps:

(1) The upper wax model is removed from the articulator and the upper plaster model is positioned and placed onto the lower wax model such that the plaster model maintains exactly the same relationship to the lower wax model as the upper wax model which has been removed. At this point, the upper model is made of plaster and the lower model has the teeth positioned in wax.

(2) Plaster is poured on the top of the plaster upper model and the articulator closed such that, when the plaster dries, the upper plaster model is attached to the articulator.

(3) The lower wax model is removed from the articulator and replaced with the lower plaster model of step (h) by placing and positioning the lower plaster model in alignment with the upper model now attached to the articulator in the manner as described above. Plaster is then poured over the surface of the lower plaster model, the articulator closed and upon drying of the plaster, the lower model becomes attached to the articulator.

(j) Opening the articulator to form a space of from 3 to 5 mm between the upper and lower incisor edge.

Again, this space is necessary to properly form the silicone resin treating device as previously discussed in step (i) of the first procedure.

(k) Forming heat-curable silicone resin around the upper and lower teeth and curing the resin.

Soft silicone resin is pressed by hand over the entire surface areas of the teeth, front and back, and between the upper and lower teeth to fill the space created in the previous step. The resin is shaped to the final form of the treating device by trimming any excess material. The entire assembly is then subjected to heat such as placing in the boiling water for about 40 minutes to cure the resin. It is to be understood that in either procedure of the present invention, the resin may be cured by heating to a temperature of 100° to 130° C. by means of, for example, boiling water or hot air.

(l) Removing the resulting treating device.

After curing of the resin, the entire assembly of the plaster model having applied thereto the silicone resin material is cooled, the articulator opened and the resulting treating device removed from the plaster cast.

The device may then be coated with the two-component silicone resin solution as described above to provide a final product having a smooth finish.

Various types of silicone resin materials may be employed in the present invention, provided that they have the proper physical properties for moving a patient's teeth from malocclusion to normal occlusion. The properties provided by the silicone resin materials as employed in the present invention include resins which are easily curable by subjecting to heat in the temperature range of from 100° to 130° C., have no odor, taste or any chemical ingredients that would be harmful to the body. In addition, the resins of the present invention are transparent such that the patient's teeth and gums can be observed through the treating device during treatment.

The silicone resin materials employed in the present invention are prepared in a composition containing (a) a silicone resin base material and (b) a catalyst including an oil such as silicone oil. Although various types of silicone resin materials may be employed having the properties as discussed above, examples include materials having the formula:

The catalyst employed in the silicone resin composition includes those represented by the following formula:

(b)

The catalyst composition includes an oil such as silicone oil. The catalyst composition contains from about 40 to about 50% of the catalyst and from about 50 to about 60% of the oil. The ratio of the silicone resin material to the catalyst composition may be about 100 g of (a) to from about 1 to about 2 g of (b), respectively.

The silicone resin composition may be prepared by mixing together (a) and (b) in a mixer for a time sufficient to obtain a complete physical blend of the materials. The resulting composition may then be stored in a cool area such as a refrigerator.

The properties of the silicone resin material to be employed in the present invention are as follows:
(1) Hardness (JIS): about 40 to about 60
(2) Tensile strength: about 85 to about 130 kg/cm$^2$
(3) Strain: about 400 to about 560%
(4) Molecular weight: about $6 \times 10^5$ (base silicone)
(5) 200% modulus: about 35 to about 45 kg/cm$^2$ FIG. 1 shows the original plaster model after taking an impression of the malocclusion of a patient to be treated including teeth 1 also made of plaster.

Figure 1:
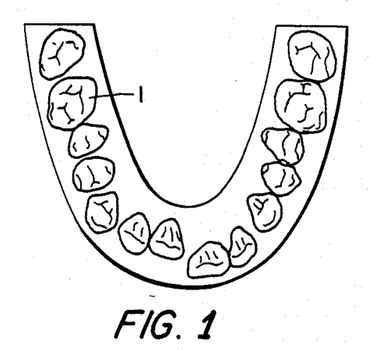
FIG. 1 is an occlusal view of an original model with malocclusion.
Figure 2:
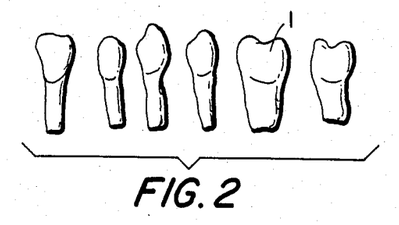
FIG. 2 is an elevation of several teeth separated from the model of FIG. 1.
Figure 3:
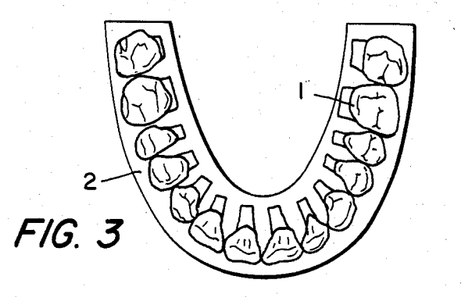
FIG. 3 is an occlusal view of a model obtained by rearranging in wax the teeth from the original model to a normal occlusion.
Figure 4:
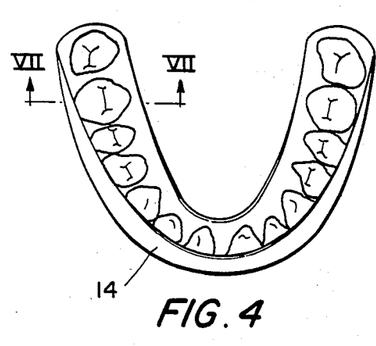
FIG. 4 is a occlusal view of the complete orthodontic treating device.
Figure 5:
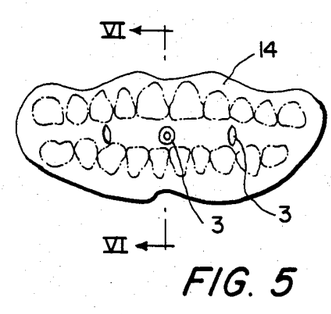
FIG. 5 is a front elevation of the orthodontic treating device.

FIG. 2 shows the respective teeth removed from the original model of FIG. 1, and FIG. 3 shows the condition where the teeth are rearranged into the normal occlusion using wax 2 employed for mounting and fixing the teeth. FIG. 4 shows the complete orthodontic treating device using silicone resin 14 as blank material, and FIG. 5 shows the device having ventilation holes 3 for respiration and the teeth shown by dotted lines are negative impressions of the teeth which are rearranged to the normal occlusion. The malaligned teeth of the patient to be treated are inserted into the device having the negative impressions by the patient closing his jaws together. When the silicone resin device is deformed by the teeth, the restoring force of the resin is generated and the correcting force causes the teeth to shift to the normal occlusion of the device.

Figure 6:
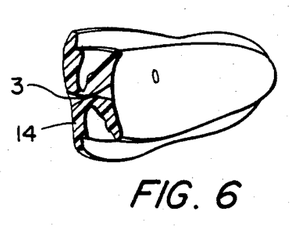
FIG. 6 is a cross sectional view taken along a line VI—VI in FIG. 5.
Figure 7:
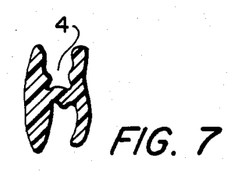
FIG. 7 is an end cross sectional view of the cross section taken along a line VII—VII in FIG. 4.
Figure 8A:
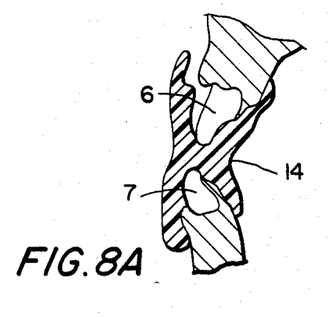
Figure 8B:
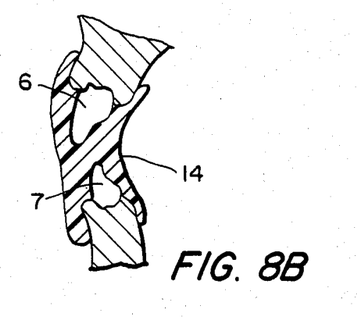

FIG. 6 is a cross sectional view taken along a line VI—VI of the preceding drawing, and FIG. 7 is an end sectional view taken along a line VII—VII of FIG. 4 showing a concave mold 4 of the device for insertion of a molar of the upper jaw, and a concave mold 5 for a molar of the lower jaw. FIG. 8 is a comparison drawing showing the conditions before and after the orthodontic treatment with the device of the invention, and 8A shows before the orthodontic treatment and 8B shows after the orthodontic treatment and also showing an anterior tooth 6 of the upper jaw, and an anterior tooth 7 of the lower jaw. FIG. 8A shows gaps on the lip side of the upper anterior tooth and on the tongue side of the lower anterior tooth. FIG. 8B does not show the gap due to the movement of the tooth with the orthodontic force generated from the restoring force of the resin during the treatment.

Figure 9A:
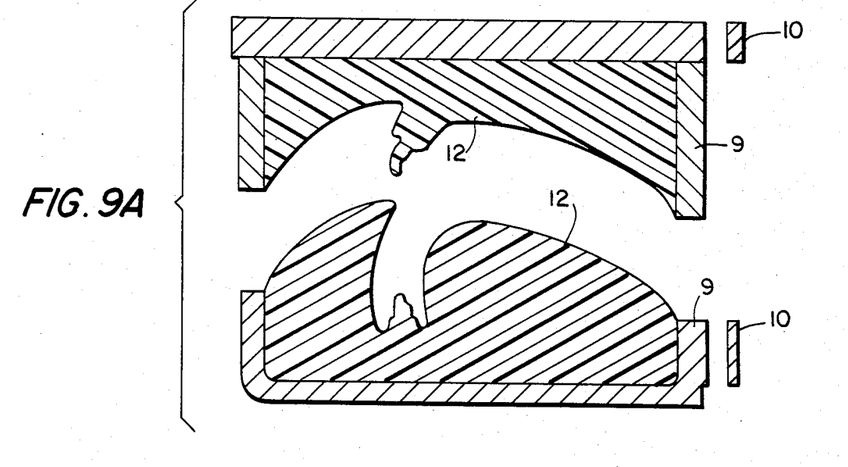
Figure 9B:
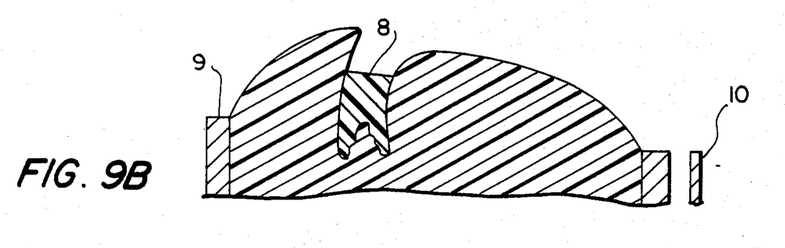
Figure 9C:
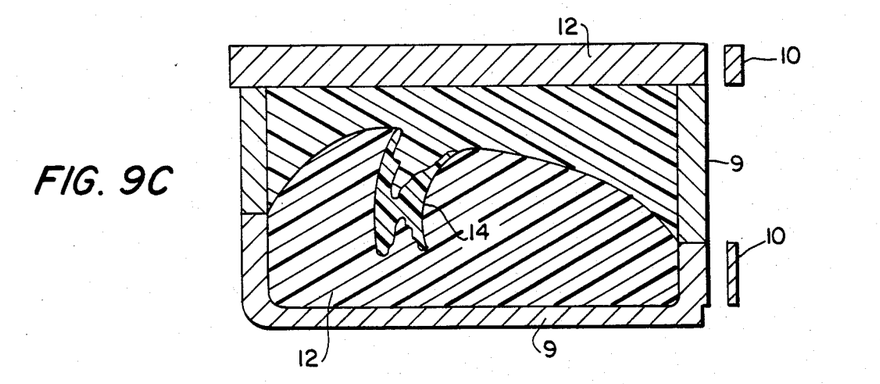
Figure 10A:
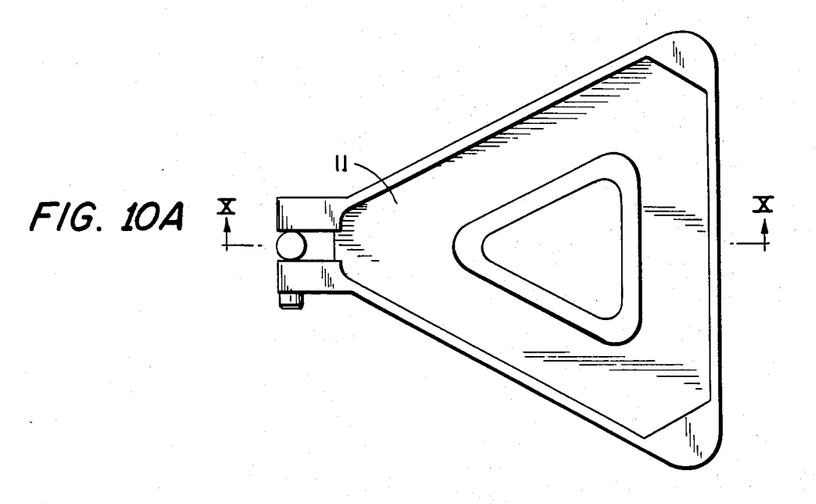
Figure 10B:
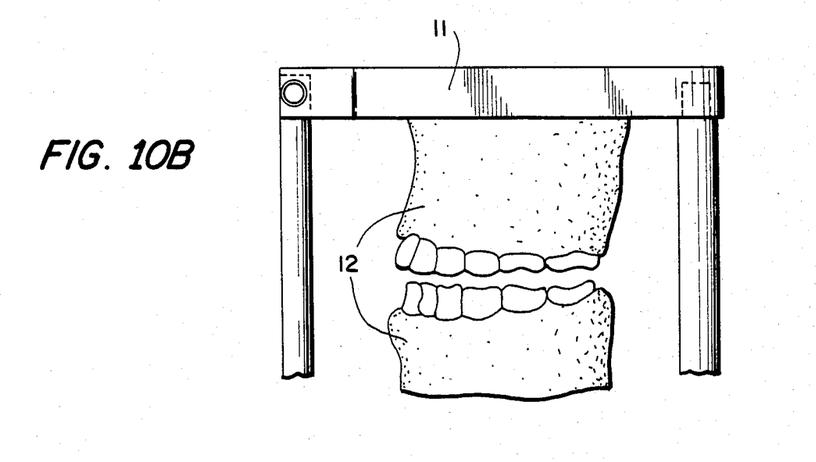
Figure 10C:
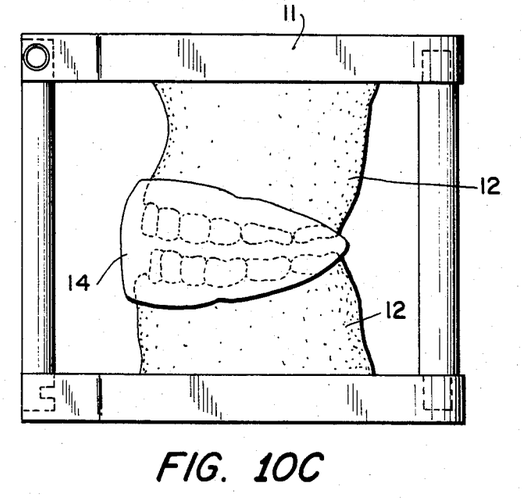
Figure 10D:
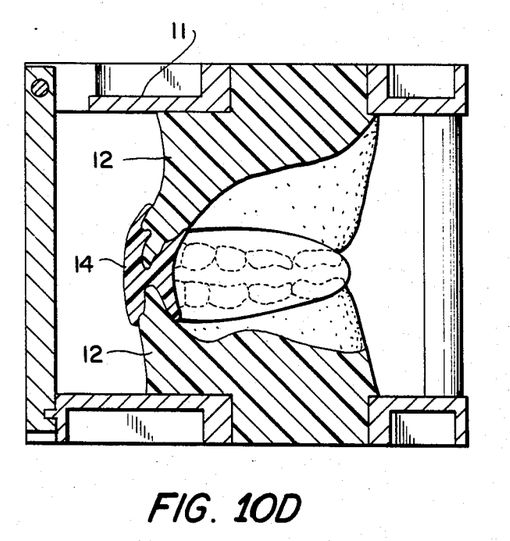

FIG. 9 shows the first embodiment of the present invention, and 9A shows the condition where the split-cast 9 is separated and contains the plaster models with the teeth in normal occlusion embedded in plaster 12, and 9B shows the condition where the silicone resin 8 is filled or poured into the lower half portion of the split-cast, and 9C shows the condition where the separated split-cast are joined and the silicone resin 8 completely surrounds the teeth, and 10 denotes a connecting member for the split-cast.

FIG. 10 shows the second embodiment of the present invention, and 10A is a top view of the anatomical articulator 11, and 10B is the side view thereof, showing the condition where the wax plate is melted and discharged, and in this conditional position, the silicone resin is pressure contacted and molded over the plaster models to form the orthodontic treating device. The drawing 10C is a side view of the orthodontic treating device formed with the silicone resin, and when this device is cured by hot water or hot air, a final product is formed. FIG. 10D is a cross sectional view taken along a line X—X of the 10A. The number 12 denotes a working model, and number 14 denotes the orthodontic treating device.

The silicone resin treating device as prepared above has negative impressions or voids which duplicate the patient's teeth and move the teeth to a desired position such as normal occlusion during treatment. Complete orthodontic treatment is accomplished by (a) opening the patient's mouth to expose the upper and lower jaws and teeth, (b) fitting the device by using finger pressure to force the device over the upper teeth, and (c) closing the lower jaw to force the device over the lower teeth. The actual movement of the teeth is accomplished by (d) forcing or clenching the upper and lower teeth together for short periods of time, preferably from about 10 to 20 seconds to cause the device to place pressure or force against the teeth, relaxing the jaws to relieve the pressure and repeating the clenching and relaxing during the patient's waking hours, (e) retaining the device over the patient's teeth during sleeping hours, and (f) repeating steps (d) and (e) for a period of time sufficient to move the teeth to the desired position.

It is to be understood that where the malocclusion is severe such that the teeth must moved considerable distances, it may be necessary to use several treating devices of the invention such that the teeth may be moved short distances with each treatment in accordance with the above treatment procedures. Furthermore, where several devices are necessary for treatment, each device can be prepared in accordance with the above-described procedures.

The orthodontic treating device obtained according to the present invention produces a normal occlusion on the basis of the rearranged teeth of the patient. As the teeth are gradually corrected after placing it in the mouth, it renders no undue stress to the teeth or the periodontal structure, causing the correcting force of the device to work and, as a result, the orthodontic treatment is accomplished.

Because of its properties, the orthodontic treating device molded from silicone resin cannot be permanently deformed and is free from changes due to stress. Its hardness can be changed freely and it can be made transparent without taste and odor, whereby it has advantageous points that it provides not only an excellent orthodontic treatment but also ease of use on the part of the patient.

Particularly, the present invention is advantageous in comparison with known polyurethane resins, since the time for polymerizing the polyurethane is about 20 minutes and therefore the present invention shortens the manufacturing time tremendously. Also, the polyurethane resin produces foam of carbonic acid gas in large quantities when reacted with the water in the plaster and, therefore, the working model has to be manufactured by using special resins, and it has the drawback of producing deformations due to the great shrinkage resulting from heat curing the resin. Therefore, in the case of using silicone resin of the present invention, plaster can be used to make the working model and absolutely no deformation occurs and, as a result, the orthodontic treating device can be produced with improved accuracy.

Furthermore, in using polyurethane resins, handling of the undiluted liquid is attended with danger, and also defoaming during the stirring process with a vacuum pump is needed to prevent the foaming of the polyurethane. Also, a high pressure compressor and an autoclave must be used, and, moreover, in the molding, a large size grinder is required, so there are complicated operation processes and inconveniences of using special machines. On the contrary, the present invention is extremely safe, since it employs the silicone resin, eliminating the defoaming during the stirring process and polishing and finishing procedures, and, accordingly, it has many excellent effects.

What is claimed is:

1. A method of manufacturing a silicone resin orthodontic treating device which comprises
    (a) preparing plaster models of a patient's upper and lower jaw including the teeth showing malocclusion,
    (b) determining the centric relationship between the patient's upper and lower teeth by taking a wax impression,
    (c) taking a face-bow transfer of the patient's upper teeth to establish and reproduce the relationship of upper jaw to the head and face,
    (d) placing the face-bow in an anatomical articulator,
    (e) positioning the upper and lower models of step (a) in the anatomical articulator using the face-bow and wax bite of step (b) to reproduce the patient's upper and lower jaw relationship and fixing the models in plaster such that the models are attached to the articulator,
    (f) removing the teeth from the models and re-aligning the teeth in wax to normal occlusion,
    (g) duplicating the normal occlusion of the models with a duplicating material to form negative impressions,
    (h) forming positive plaster models from the negative impressions,
    (i) opening the articulator to form a space of from 3 to 5 mm between the upper and lower incisor edge,
    (j) placing wax in the space to obtain an impression of the upper and lower teeth in normal occlusion,
    (k) placing the teeth of the upper and lower plaster models of step (h) into the wax impression of step (j),
    (l) covering the resulting combination of step (k) with wax such that the wax will have substantially the same shape and thickness as the silicone resin treating device,
    (m) flasking the wax covered model combination of step (l) in a split-cast,
    (n) subjecting the split-cast containing the wax covered model to heat sufficient to melt the wax and produce a void,
    (o) removing the wax,
    (p) filling the void with a hot-curable silicone resin and curing the resin, and
    (q) removing the silicone resin treating device.

2. The method according to claim 1 wherein the resin is cured at a temperature of from about 100° C. to about 130° C.

3. The method of claim 1 wherein the silicone resin is a composition containing
    (a) a silicone resin having the following formula (b) a catalyst composition containing
        (1) a compound having the formula (2) a silicone oil.

4. A method of manufacturing a silicone resin orthodontic treating device which comprises
    (a) preparing plaster models of a patient's upper and lower jaw including the teeth showing malocclusion,
    (b) determining the centric relationship between the patient's upper and lower teeth by taking a wax impression,
    (c) taking a face-bow transfer of the patient's upper teeth to establish and reproduce the relationship of upper jaw to the head and face,
    (d) placing the face-bow in an anatomical articulator,
    (e) positioning the upper and lower models of step (a) in the anatomical articulator using the face-bow and wax bite of step (b) to reproduce the patient's upper and lower jaw relationship and fixing the models in plaster such that the models are attached to the articulator,
    (f) removing the teeth from the models and re-aligning the teeth in wax to normal occlusion,
    (g) duplicating the normal occlusion of the models with a duplicating material to form negative impressions,
    (h) forming positive plaster models from the negative impressions,
    (i) removing the wax models from the articulator and replacing them with the plaster models of step (h) while maintaining the same upper and lower jaw relationship,
    (j) opening the articulator to form a space of from 3 to 5 mm between the upper and lower incisor edge,
    (k) forming heat-curable silicone resin around the upper and lower teeth and curing the resin, and
    (l) removing the resulting treating device.

5. The method according to claim 4 wherein the resin is cured at a temperature of from about 100° C. to about 130° C.

6. The method of claim 4 wherein the silicone resin is a composition containing
    (a) a silicone resin having the following formula (b) a catalyst composition containing (1) a compound having the formula (2) a silicone oil.